(12) United States Patent
Helland

(10) Patent No.: US 8,108,054 B2
(45) Date of Patent: Jan. 31, 2012

(54) ACTIVE FIXATION IMPLANTABLE MEDICAL LEAD CONFIGURED TO INDICATE VIA FLUOROSCOPY EMBEDMENT OF HELICAL ANCHOR IN CARDIAC TISSUE

(75) Inventor: John R. Helland, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 210 days.

(21) Appl. No.: 12/365,522

(22) Filed: Feb. 4, 2009

(65) Prior Publication Data
US 2010/0198327 A1  Aug. 5, 2010

(51) Int. Cl.
*A61N 1/00* (2006.01)
(52) U.S. Cl. ........................................ 607/127
(58) Field of Classification Search ........ 607/116, 607/119, 126–127, 131
See application file for complete search history.

(56) References Cited

U.S. PATENT DOCUMENTS

| | | | | |
|---|---|---|---|---|
| 3,902,501 A * | 9/1975 | Citron et al. | ........ | 607/126 |
| 4,649,938 A * | 3/1987 | McArthur | ........ | 607/127 |
| 4,815,478 A * | 3/1989 | Buchbinder et al. | ........ | 600/585 |
| 4,972,848 A * | 11/1990 | Di Domenico et al. | ........ | 607/127 |
| 5,002,067 A * | 3/1991 | Berthelsen et al. | ........ | 607/120 |
| 5,020,545 A * | 6/1991 | Soukup | ........ | 607/127 |
| 5,259,395 A * | 11/1993 | Li | ........ | 607/131 |
| 5,300,108 A * | 4/1994 | Rebell et al. | ........ | 607/127 |
| 5,313,967 A * | 5/1994 | Lieber et al. | ........ | 600/585 |
| 5,324,325 A * | 6/1994 | Moaddeb | ........ | 607/120 |
| 5,374,286 A * | 12/1994 | Morris | ........ | 607/119 |
| 5,456,705 A | 10/1995 | Morris | | |
| 5,456,708 A * | 10/1995 | Doan et al. | ........ | 607/127 |
| 5,531,783 A * | 7/1996 | Giele et al. | ........ | 607/126 |
| 5,596,996 A * | 1/1997 | Johanson et al. | ........ | 600/585 |
| 5,776,178 A * | 7/1998 | Pohndorf et al. | ........ | 607/127 |
| 5,916,178 A * | 6/1999 | Noone et al. | ........ | 600/585 |
| 6,042,876 A * | 3/2000 | Deem | ........ | 427/2.28 |
| 6,493,591 B1 * | 12/2002 | Stokes | ........ | 607/127 |
| 6,915,169 B2 | 7/2005 | Flynn et al. | | |
| 7,092,766 B1 * | 8/2006 | Salys et al. | ........ | 607/127 |
| 7,162,310 B2 | 1/2007 | Doan | | |

* cited by examiner

Primary Examiner — Eric D Bertram
Assistant Examiner — Roland Dinga

(57) ABSTRACT

An implantable medical lead for active fixation to cardiac tissue is disclosed herein. The lead may include a lead body distal end, a tissue fixation helical anchor and a structure. The tissue fixation helical anchor may be coupled to the lead body distal end and include a distal tip. The structure may be coupled to the lead body distal end and include a structure distal end including a first radiopaque marker. The structure may be biased to project the structure distal end near the distal tip. When the tissue fixation helical anchor is progressively embedded in the cardiac tissue, the cardiac tissue progressively displaces the structure distal end proximally.

16 Claims, 7 Drawing Sheets

ACTIVE FIXATION IMPLANTABLE MEDICAL LEAD CONFIGURED TO INDICATE VIA FLUOROSCOPY EMBEDMENT OF HELICAL ANCHOR IN CARDIAC TISSUE

FIELD OF THE INVENTION

The present invention relates to medical apparatus and methods. More specifically, the present invention relates to implantable medical leads and methods of manufacturing such leads.

BACKGROUND OF THE INVENTION

Current active fixation pacing and ICD leads typically employ a tissue fixation helical anchor. Such helical anchors are well known in the art, are the most utilized fixation configuration in cardiac leads, and have been utilized in implantable cardiac leads in cardiac rhythm disease management systems for over 30 years.

A helical anchor is typically located in the distal end of the lead and is mechanically coupled to a shaft within a distal portion of the lead. The shaft is mechanically coupled to the inner coil conductor, which extends through the lead to the lead connector end at the lead proximal end, the lead connector end being configured to mechanically couple to a pulse generator such as, for example, a pacemaker or implantable cardioverter defibrillator ("ICD"). A pin contact extending proximally from the lead connector end is mechanically coupled to the inner coil conductor. The helical anchor, shaft, inner conductor coil and pin contact are rotatable as a unit relative to the rest of the lead and lead connector end.

A helical anchor is typically deployed (i.e., extended from within the lead distal end) and fixated into the cardiac tissue by rotation of the pin contact relative to the rest of the lead connector end in a direction such as, for example, a clockwise direction. Thus, when it is desired to achieve fixation of the lead distal end to the implantation site, the physician rotates the connector pin clockwise relative to the rest of the lead connector end, thereby causing the helical anchor to extend out of the lead distal end and screw into the tissue.

An ongoing difficulty with active fixation leads employing helical anchors a physician has no reliable way to determine exactly when the helical anchor is fully embedded into the cardiac tissue at the desired implantation site. Since it is not possible to determine via fluoroscopy when the helical anchor is fully embedded into the cardiac tissue, it is common for a physician to fail to fully embed the helical anchor into the cardiac tissue. Indeed, only a portion of the helical anchor may actually be embedded, resulting in a high risk for dislodgement of the helical anchor from the tissue, which would then render the lead incapable of delivering the intended electrical therapy. Additionally, a helical anchor electrode that is not fully embedded into the cardiac tissue may also cause increased tissue damage to the local tissue adjacent to the helical anchor electrode, thereby resulting in deterioration of the electrical parameters (e.g., pacing capture thresholds, sensing of cardiac signals, etc.).

The opposite situation can also occur and cause therapy malfunction. That is, the physician, not knowing if the helical anchor is fully embedded into the desired cardiac tissue, may either over-rotate the connector pin numerous additional rotations ("over-torqueing the helical anchor") or may rotate the whole lead body to try and "tighten-up" the helical anchor into the tissue. The result of such "over-torqueing" can be damage to the lead and, more specifically, the connections (e.g., welds, etc.) between the pin contact and inner conductor coil, the inner conductor coil and the shaft, or the shaft and the helical anchor. The result of such "over-torqueing" can also be compression of the tissue initially, subsequent coring of the cardiac tissue by the helical anchor, much like a wine bottle corkscrew can "chew-up" the cork when it is over rotated into the cork and the handle is bottomed-out against the bottle top. This compression and ultimately the "coring" of cardiac tissue at an implantation site with via a helical anchor of a lead is well described by T. Laske, et. al; in PACE, September, 2005, pg 887. Such coring can significantly increase the risk for damaged tissue at the helical anchor site, resulting in deterioration of the lead's electrical parameters and ultimately the lead's distal tip has a much higher risk of perforating the heart wall.

There is a need in the art for a lead configured to allow for determining whether or not the helical anchor is fully embedded in the cardiac tissue of the desired implantation site.

BRIEF SUMMARY OF THE INVENTION

An implantable medical lead for active fixation to cardiac tissue is disclosed herein. In one embodiment, the lead may include a lead body distal end, a helical anchor and a structure. The helical anchor may be coupled to the lead body distal end and include a distal tip. The structure may be coupled to the lead body distal end and include a structure distal end including a first radiopaque marker. The structure may be biased to project the structure distal end near the distal tip. When the helical anchor is progressively embedded in the cardiac tissue, the cardiac tissue progressively displaces the structure distal end proximally.

An implantable medical lead for active fixation to cardiac tissue is disclosed herein. In one embodiment, the lead may include a lead body distal end including a first radiopaque marker, a helical anchor and a second radiopaque marker. The helical anchor may be coupled to the lead body distal end and include a distal tip. The second radiopaque marker may be operably coupled to the lead body distal end. When the helical anchor is progressively embedded in the cardiac tissue, the cardiac tissue progressively displaces the second radiopaque marker from a location near the distal tip towards a location near the first radiopaque marker.

A method for implanting an implantable active fixation medical lead is also disclosed herein. In one embodiment, the method may include: deliver a distal end of a lead body to the implantation site; observe via fluoroscopy the presence of a first radiopaque marker near a distal tip of a helical anchor; and observe via fluoroscopy the proximal displacement of the first radiopaque marker as the helical anchor is screwed into cardiac tissue.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
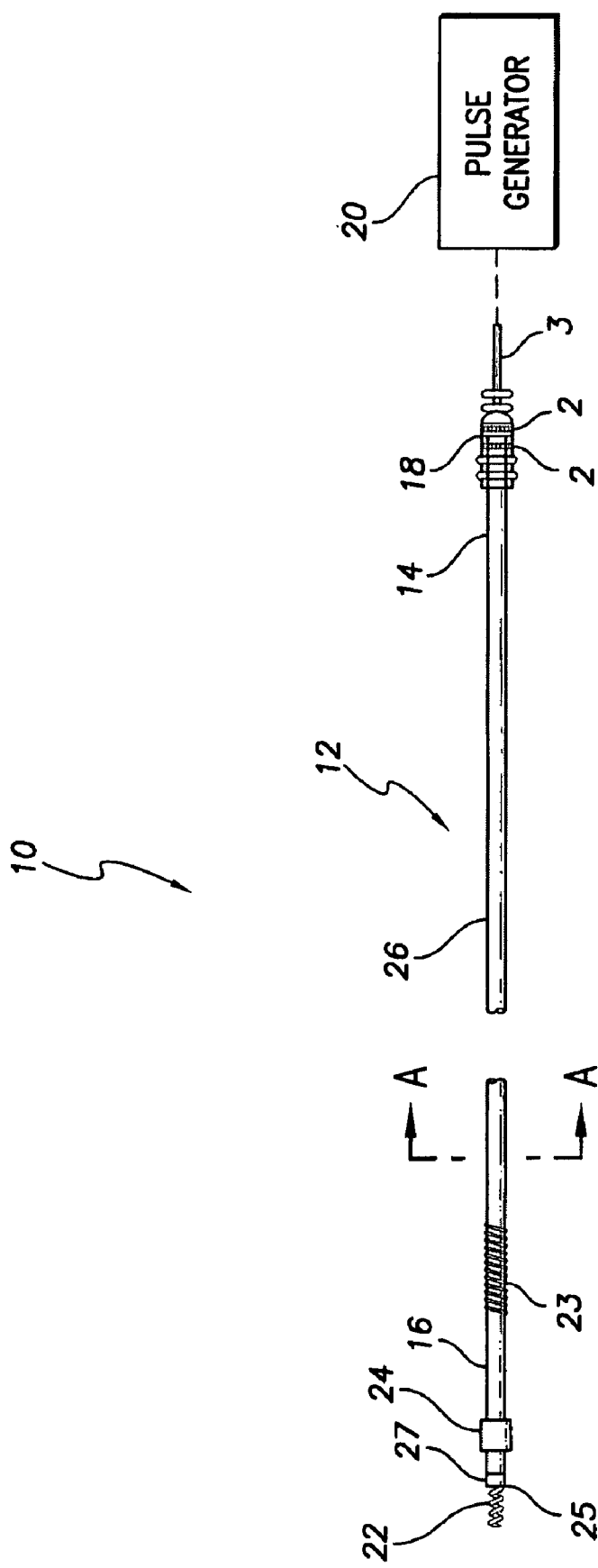
FIG. 1 is a side view of an electrophysiology device and, more specifically, an active fixation implantable medical lead.

An implantable active fixation medical lead 10 is disclosed herein. In one embodiment, the lead 10 includes a feature 32, 100 at a distal tip 25 of the lead 10 that allows an implanting physician to determine via fluoroscopy when a helical anchor 22 is fully embedded into the cardiac tissue at the desired implantation site. In one embodiment, the feature 32 may include one or more protuberances 32 with radiopaque markers 44 at the protuberance tips 34 and which move increasingly proximally via contact of the tips 34 with the cardiac tissue surface 40 when the helical anchor 22 is progressively screwed into the cardiac tissue 29. Upon the helical anchor 22 being fully embedded in the cardiac tissue 29, fluoroscopy will show that the radiopaque markers 44 within the protuberance tips 34 move sufficiently proximal such the radiopaque markers 44 will appear flush with other radiopaque markers 56 in the lead distal tip 25.

In another embodiment, the feature 100 may be a body with a distal end 104 that includes a radiopaque marker 46, wherein the distal end 104 and its marker 46 move increasingly proximally via contact of the distal end 104 with the cardiac tissue surface 40 when the helical anchor 22 is progressively screwed into the cardiac tissue 29. Upon the helical anchor 22 being fully embedded in the cardiac tissue 29, fluoroscopy will show that the radiopaque marker 46 within the body distal end 104 moves sufficiently proximal such the radiopaque marker 46 will appear flush with other radiopaque markers 56 in the lead distal tip 25.

The following description presents preferred embodiments of the lead and its method of manufacture and represents the best mode contemplated for practicing the lead and its method of manufacture. This description is not to be taken in a limiting sense, but is made merely for the purpose of describing the general principles of the lead and its method of manufacture, the scope of both being defined by the appended claims.

FIG. 1 is a side view of an active fixation implantable medical lead 10, which may be any type of an implantable medical lead 10, including, for example, a bradycardia, tachycardia, RV, LV or other type of lead. As shown in FIG. 1, the lead 10 includes a tubular body 12 having a proximal end portion 14 and a distal end portion 16. The proximal end portion 14 of the tubular body 12 carries a connector assembly 18 for coupling the tubular body 12 to a receptacle on a pulse generator 20 such as, for example, a pacemaker or an ICD. Depending on its type, the lead connector end 18 may include one or more ring contacts 2 and a pin contact 3, the contacts 2, 3 contacting complementary contacts in the pulse generator 20 when the lead connector end 18 is received in the pulse generator 20.

The distal end portion 16 of the tubular body 12 may carry a helical anchor 22 and a ring electrode 24 proximal of the helical anchor 22 and spaced apart therefrom. The ring electrode 24 may serve as a pacing/sensing electrode. The distal end portion 16 may also include a shock coil 23 proximal of the helical anchor 22 or the ring electrode 24 (if present) that may serve as a cardioverting and/or defibrillation electrode 23.

While FIG. 1 depicts the helical anchor 22 distally extended from the lead distal tip 25, it should be noted that the helical anchor 22 may be caused to distally extend from within the lead distal tip 25 via, for example, clockwise rotation of the contact pin 3 or be caused to retract into the lead distal tip 25 via, for example, counter clockwise rotation of the contact pin 3. Thus, the helical anchor 22 may be extended from within a distal end tip 25 of the distal end portion 16 to be screwed into cardiac tissue at a desired implantation site. The distal end portion 16 may also include a tip electrode 27 at or forming the distal end tip 25, the tip electrode 25 serving as a pacing/sensing electrode. In some embodiments, no tip electrode 27 is present, the helical anchor 22 instead serving as the tip electrode 22 in addition to acting as an active fixation mechanism. In other embodiments, the lead 10 includes both a tip electrode 27 and a helical anchor 22 that acts as an electrode and, more specifically, as part of the tip electrode 27.

The tubular body 12 may be adapted to transmit stimulating and/or sensed electrical signals between the connector assembly 18, on the one hand, and the helical anchor electrode 22, tip electrode 27, ring electrode 24, shock coil 23, and other electrodes. For example, the tubular body 12 may have one or more conductors (e.g., cable conductors, helical coil conductors, etc.) longitudinally extending through the tubular body 12 between a contact 2, 3 and a respective electrode 22, 23, 24, 27, thereby placing the contact 2, 3 and respective electrode 22, 23, 24, 27 in electrical communication. The conductors may be arranged such that they can be in a single lumen with co-radial coil conductors, or in a coaxial or tri-axial coil configuration, or in a multilumen lead body configuration with at least one conductor coils and at least one conductor cable.

By way of example and not limitation, the distal end portion 16 of the tubular body 12 of the lead 10 may have a diameter of about 0.026 inch (2F) to about 0.131 inch (10F), with a diameter of about 0.079 (6F) being preferred, and the ring electrode 24, where it serves a sensing function, may have a diameter of about 0.079 inch (6F) and a length of about 0.100 inch. The tubular body 12 may include a tubular insulating sheath or housing 26 of a suitable insulative biocompatible biostable material such as, for example, silicone rubber, polyurethane, silicone rubber-polyurethane-copolymer ("SPC") or other suitable elastomer, extending the entire length of the tubular body 12.

Figure 2:
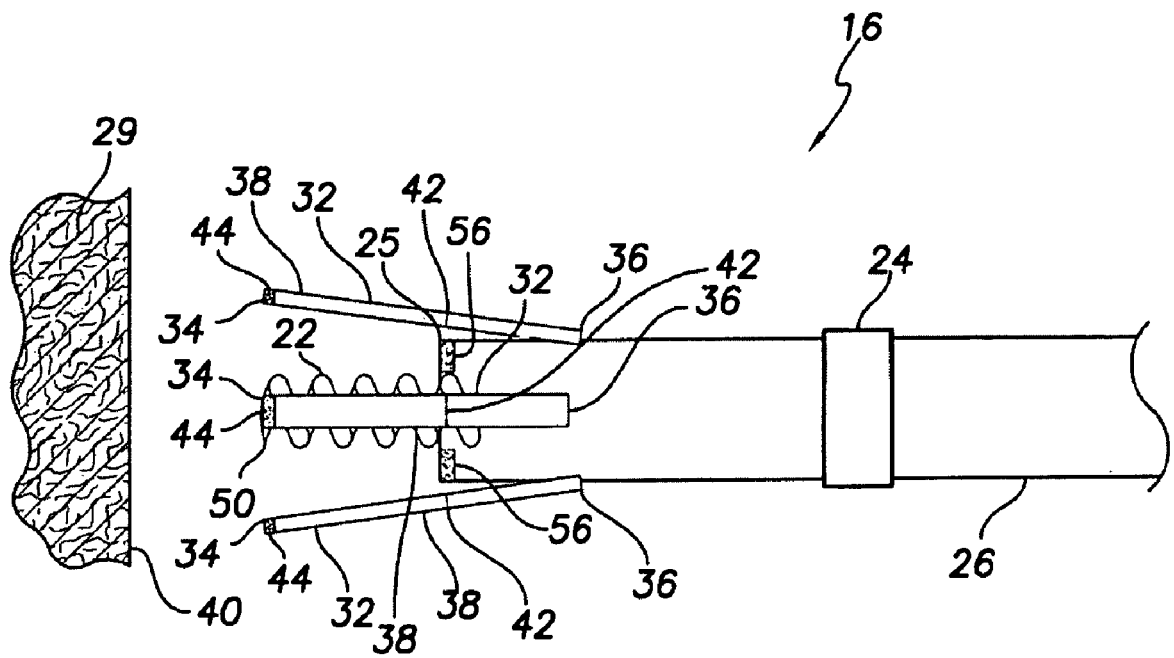
FIG. 2 is a diagrammatic side view of a lead distal portion having protuberances having radiopaque markers, wherein the helical anchor is yet to be embedded in the cardiac tissue.
Figure 3:
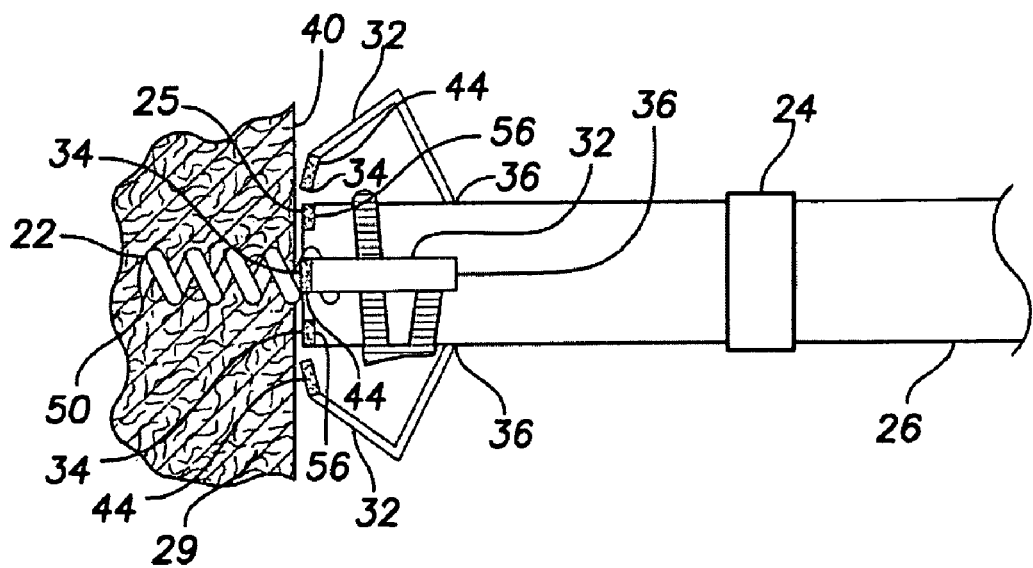
FIG. 3 is the same view as FIG. 2, except the helical anchor is embedded in the cardiac tissue.

For a detailed discussion regarding a first lead distal end configuration that facilitates a physician determining via fluoroscopy whether or not the helical anchor 22 has fully and properly embedded within the cardiac tissue, reference is made to FIGS. 2 and 3. FIG. 2 is a diagrammatic side view of a lead distal portion 16, wherein the helical anchor 22 is yet to be embedded in the cardiac tissue 30. FIG. 3 is the same view as FIG. 2, except the helical anchor 22 is embedded in the cardiac tissue 29. While FIGS. 2 and 3 depict the helical anchor 22 distally extended from the lead distal tip 25, it should be noted that the helical anchor 22 may be caused to distally extend from within the lead distal tip 25 via, for example, clockwise rotation of the contact pin 3 (see FIG. 1) or caused to retract into the lead distal tip 25 via, for example, counter clockwise rotation of the contact pin 3.

As shown in FIG. 2, in one embodiment, one or more protuberances 32 distally project off of the lead distal end 25. The protuberances 32 may each have a distal end 34, a proximal end 36, and a body or length 38 intermediate the distal end 34 and proximal end 36. The distal end 36 may be free or, alternatively, the distal ends 36 may be coupled to one or more of the distal ends 36 of the other protuberances 32 via, for example, a ring 40 as illustrated in FIG. 4, which is the same view as FIG. 2, except of another embodiment.

Figure 4:
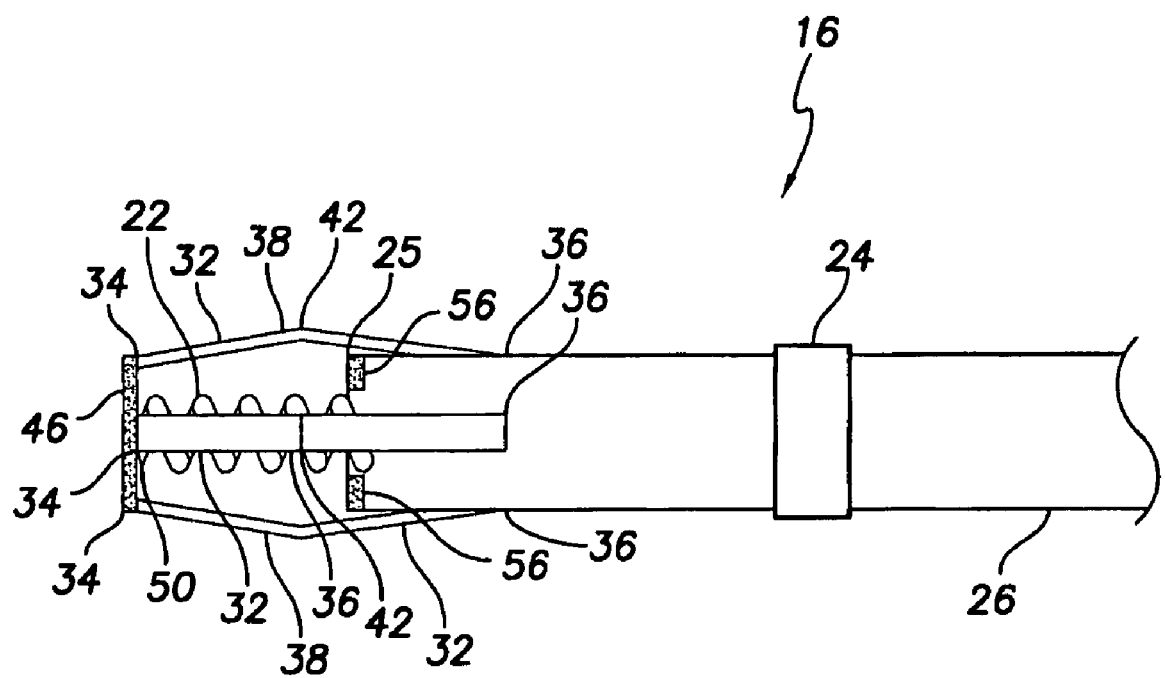
FIG. 4 is the same view as FIG. 2, except of another protuberance embodiment.

The proximal end 36 may be coupled to the lead distal portion 16, for example, at the lead distal end tip 25 or at a location proximal of the lead distal tip 25, as depicted in FIGS. 2-4. The protuberances 32 may have generally any type of shape that distally extends from the lead distal end 25 in a manner similar to that depicted in FIG. 2. For example, the protuberances 32 may be longitudinally extending members 32 such as, for example, generally flat strips or flaps or arms having cross-sections that are generally square, rectangular, circular, oval, convex, concave, triangular, elliptical or etc.

As indicated in FIG. 2, the protuberances 32 may be biased to project distally when not acted on by a force. In other words, if the helical anchor 22 has not yet encountered the surface 40 of the cardiac tissue 29 in which the helical anchor 22 is to be embedded, the protuberances 32 will project generally distally, as illustrated in FIGS. 2 and 4. In some embodiments as shown in FIGS. 2 and 4, the protuberances 32 may be biased such that the distal ends 34 project both distally and at least slightly radially inward (or outward as an alternative) when the protuberances 32 have not been acted on by a force. In such an embodiment, each protuberance 32 may have an arcuate or bent longitudinal cross section as the protuberance 32 extends between its distal end 34 and proximal end 36. In the context of a bent longitudinal cross section, as illustrated in FIGS. 2 and 4, each protuberance 32 may have an elbow or bend 42 defined in its body 38. Arcuate or bent configurations may facilitate a stress concentration in the protuberance 32 that facilitates the protuberances 32 deflecting or bending in a controlled or desired manner when encountering the cardiac tissue surface 40, as can be understood from FIG. 3.

Each protuberance 32 may be formed of a soft, pliable, biocompatible, electrically insulative, radio transparent material such as, for example, silicone rubber, polyurethane, silicone rubber-polyurethane-copolymer ("SPC"), etc. As shown in FIGS. 2 and 3, each protuberance 32 may include a radiopaque marker 44 at or defining the protuberance tip 34 that is visible via fluoroscopy. The marker 44 may be formed of such radiopaque materials as platinum, tantalum, iridium, rhodium, tungsten, barium sulfate, or etc. in the form of a tab molded into the radio transparent material or in the form of a filler material in the radio transparent material. As indicated in FIG. 4, the radiopaque marker 44 may be in the form of a radiopaque ring 46 at or defining the protuberance tips 34 and joining one or more of the protuberance tips 34.

As can be understood from FIG. 2, before the sharp distal tip 50 of the helical anchor 22 encounters the cardiac tissue surface 40, the protuberance tips 34 have yet to encounter the cardiac tissue surface 40 and, as a result, the protuberances 32 are in the non-deflected state. The radiopaque markers 44 are therefore visible via fluoroscopy as being in close vicinity to the helical anchor tip 50, indicating to the physician that the helical anchor 22 is not yet embedded in the cardiac tissue 29.

As the helical anchor 22 is increasingly embedded into the cardiac tissue 29, the cardiac tissue surface 40 deflects the protuberances tips 34 increasingly proximally relative to the helical anchor tip 50 until the protuberance tips 34 are located near the proximal end of the helical anchor 22 or near the lead distal tip 25, which may be visible via fluoroscopy on account of a distal tip electrode 27 (see FIG. 1) defining the lead distal tip 25 or another radiopaque marker 56 located in or defining the lead distal tip 25, as shown in FIGS. 2-4. Once the radiopaque markers 44 are fully displaced proximally relative to the anchor tip 50 via the cardiac tissue surface 40 as the helical anchor 22 is fully embedded in the cardiac tissue 29, as shown in FIG. 3, the markers 44 being in close vicinity to the proximal end of the helical anchor tip 50 or to the tip electrode 27 or radiopaque marker 44 indicates to the physician that the helical anchor 22 is fully embedded in the cardiac tissue 29. The physician may determine such a state since the radiopaque markers 44, helical anchor 22, tip electrode 27 and radiopaque markers 56 are visible via fluoroscopy and the protuberance tips 34 are deflected as shown in FIG. 3 when the helical anchor 22 is fully embedded.

Figure 5:
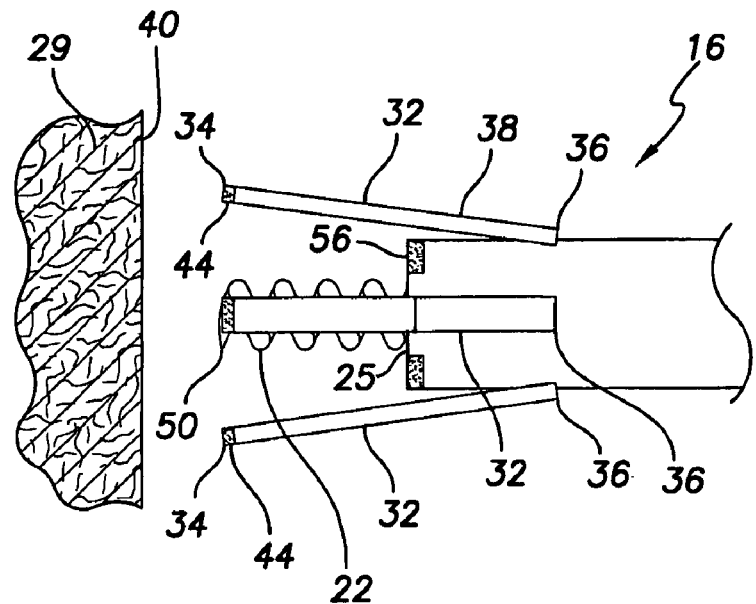
FIG. 5 is the same view as FIG. 2, except of another protuberance embodiment.
Figure 6:
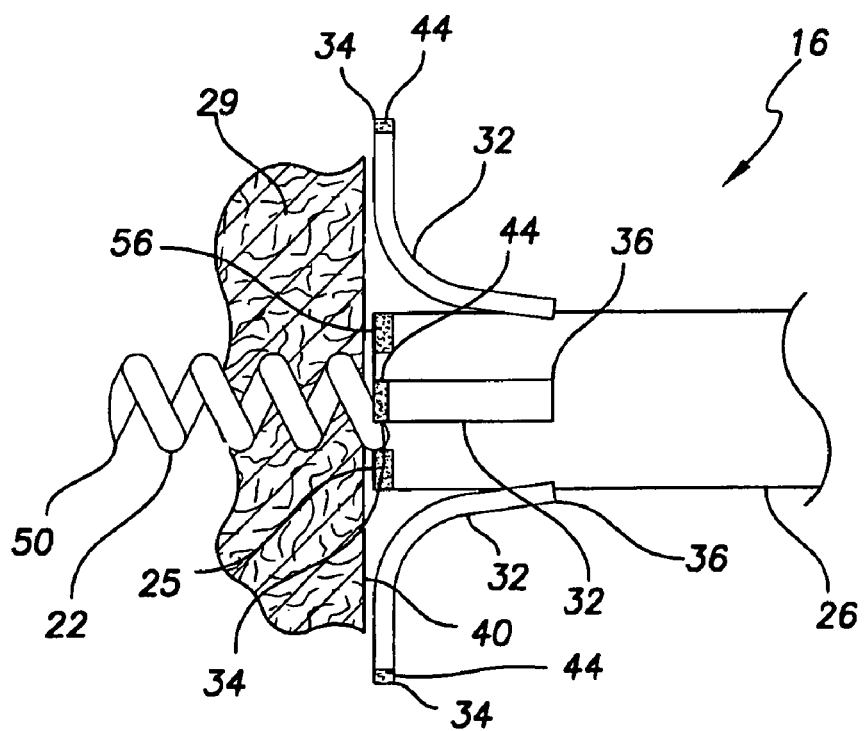
FIG. 6 is the same view as FIG. 3, except of another protuberance embodiment.

As can be understood from FIGS. 2 and 3, where the protuberances 32 have a bend 42 or a longitudinal cross section that provides a stress concentration or biases the protuberances 32 to deflect in a desired manner, the protuberances 32 may, in a fully proximally deflected state, curve such that the protuberance tips 34 are located in close proximity to the lead distal tip end 25, deflecting radially inward instead of radially outward. However, as depicted in FIGS. 5 and 6, which are the same views as FIGS. 2 and 3, except of another embodiment, the protuberances 32 may be configured such that the protuberance tips 34 deflect radially outward when deflected proximally relative to the anchor 22 by the anchor 22 being embedded in cardiac tissue 29. For example, as indicated in FIG. 5, the protuberances 32 may be configured to bias so as to project distally and radially outward when in not deflected via a force such as, for example, coming into contact with the cardiac tissue surface 40. As can be understood from FIG. 6, when the helical anchor 22 is being increasingly embedded into the cardiac tissue 29, the protuberances 32 are increasingly deflected proximally and radially outward until the markers 44 at the tips 34 are generally proximally-distally even with the markers 56 when the helical anchor 22 is fully embedded and the distal tip 25 abuts or nearly abuts the cardiac tissue surface 29.

As can be understood from FIGS. 2-6, in some embodiments, with the exception of the radiopaque markers 44, 46 at the tips 34 of the protuberances 22, the markers 44, 46 being visible via fluoroscopy, the rest of the protuberances 22 are generally invisible via fluoroscopy due to being formed of non-radiopaque materials such as, for example, silicone rubber, polyurethane, SPC, etc. In other embodiments, generally the entirety of the protuberances 22 may be radiopaque and visible via fluoroscopy due to being formed of non-radiopaque materials such as, for example, silicone rubber, polyurethane, SPC, etc., that are loaded with radiopaque materials such as tungsten, barium sulfate, etc.

Those skilled in the art will readily understand that a whole host of configurations may be employed as protuberances 32 besides those discussed above with respect to FIGS. 2-6. Accordingly, this disclosure should not be limited to those specific above-discussed configurations but should be considered to embrace all protuberance configurations that may provide the function and outcome of the above-described protuberances.

Figure 7:
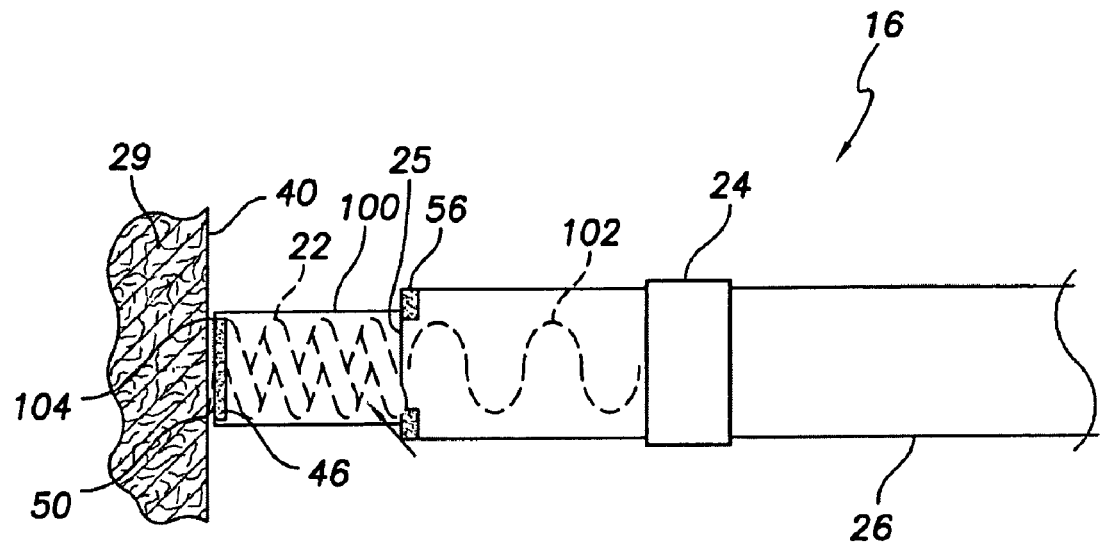
FIG. 7 is a diagrammatic side view of a lead distal portion having a body having radiopaque markers, wherein the helical anchor is yet to be embedded in the cardiac tissue.
Figure 8:
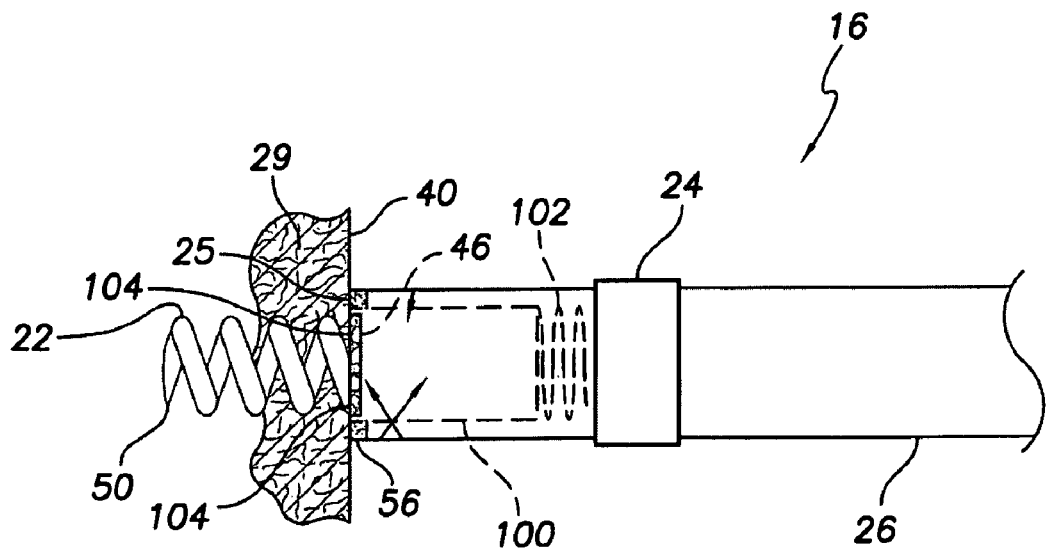
FIG. 8 is the same view as FIG. 7, except the helical anchor is embedded in the cardiac tissue.

In addition to the above-described protuberances 32, other lead distal tip embodiments may alternatively utilize configurations that may communicate to a physician via fluoroscopy that a helical anchor is fully and properly embedded in the cardiac tissue. For example, as indicated in FIGS. 7 and 8, which are the same respective views as FIGS. 2 and 3, except of another embodiment, the lead distal portion 16 may include a body 100 that has a radiopaque marker 46 at its extreme distal end. The marker 46 may be in the form of a continuous ring or a plurality of ring segments formed of a radiopaque material such as, for example, platinum, tungsten, barium sulfate, etc.

Depending on the embodiment, the body 100 may have a variety of shapes and configurations. In one embodiment, the body 100 is generally a hollow cylinder formed from a soft, atraumatic material, such as, for example, silicone rubber, polyurethane, SPC, etc. As can be understood from FIGS. 7 and 8, the body 100 may have a diameter sufficiently large so as to allow the body 100 to extend around and pass over the outer circumference of coils of the helical anchor 22, but sufficiently small to be received within the lead body housing 26. As can be understood from FIG. 7, the body 100 may be biased via a biasing member 102 (e.g., a helical spring, etc.) that causes the body 100 to be distally biased such that the distal end 104 of the body 100 with its marker 46 is located near the helical anchor tip 50 until the distal end 104 encounters the cardiac tissue surface 40 and is proximally displaced thereby. As indicated in FIG. 8, as the helical anchor 22 is increasingly embedded in the cardiac tissue 29, the cardiac tissue surface 40 increasingly proximally displaces the body distal end 104 until the body distal end 104 is near the lead housing distal end 25, such a condition existing when the helical anchor 22 is fully and properly embedded in the cardiac tissue 29. Full and proper embedding of the helical anchor 22 in the cardiac tissue 29 may be detected by the physician via fluoroscopy due to the radiopaque markers 46, 56 being in close proximity, as shown in FIG. 8. In some embodiments, when the anchor 22 is fully embedded in the cardiac tissue 29, the biasing member 102 sufficiently distally biases the body distal end 104 against the cardiac tissue surface 40 to enhance the anchoring of the anchor 22 in the cardiac tissue 29.

Figure 9:
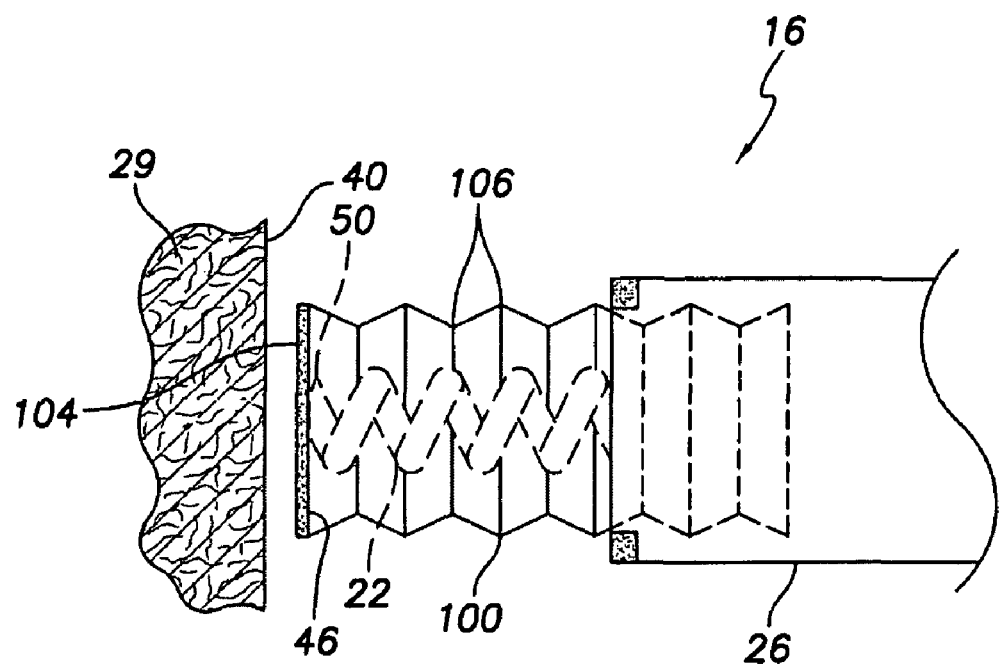
FIG. 9 is the same view as FIG. 7, except of another body embodiment.

While FIGS. 7 and 8 depict a body 100 that is biased distally via a separate biasing member 102, in other embodiments, the body 100 may be self biasing. For example, as can be understood from FIGS. 9 and 10, which are the same views as FIGS. 7 and 8, except of another embodiment, the body 100 may be self folding, pleated or accordion-like in configuration such that its side walls have a plurality of transverse seams 106 that allow the body 100 to longitudinally fold upon its plurality of seams 106 to substantially reduce the overall length of the body 100. As shown in FIG. 9, prior to being forced proximally by its distal end 104 encountering the cardiac tissue surface 40 when the helical anchor 22 is being progressively embedded in the cardiac tissue 29, the accordion-like body 104 is biased to assume an extended length whereby the body distal end 104 and its marker 46 are located near the helical anchor's tip 50. As the anchor 22 is progressively embedded in the cardiac tissue until fully the anchor is fully embedded, the body distal end 104 is progressively proximally driven via contact with the cardiac tissue surface until the body distal end and its marker 46 are near the lead housing distal end 25 and its markers 56, thereby indicating to a physician via fluoroscopy that the helical anchor 22 is fully and properly embedded in the cardiac tissue 29. As with the biasing of the separate biasing member 102 depicted in FIGS. 7 and 8, the biasing of the accordion-like body 100 may enhance the ability of the anchor 22 to remain fully embedded in the cardiac tissue.

Figure 10:
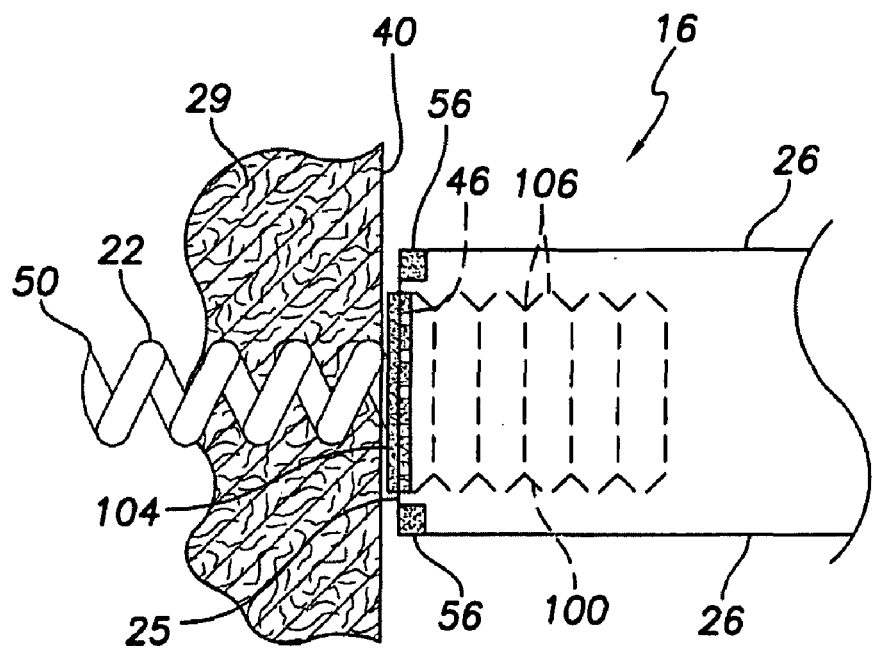
FIG. 10 is the same view as FIG. 8, except of another body embodiment.

In an alternative embodiment, instead of folding back generally completely inside of the lead housing distal end as depicted in FIG. 10, the bodies 100 may also be designed to fold-up and reside at the edge of the lead housing distal end 25, forming a cushion which is a larger diameter than the lead housing end in a manner similar to that depicted in FIG. 6 and which can help reduce the lead's tip pressure on the endocardial heart tissue.

Figure 11:
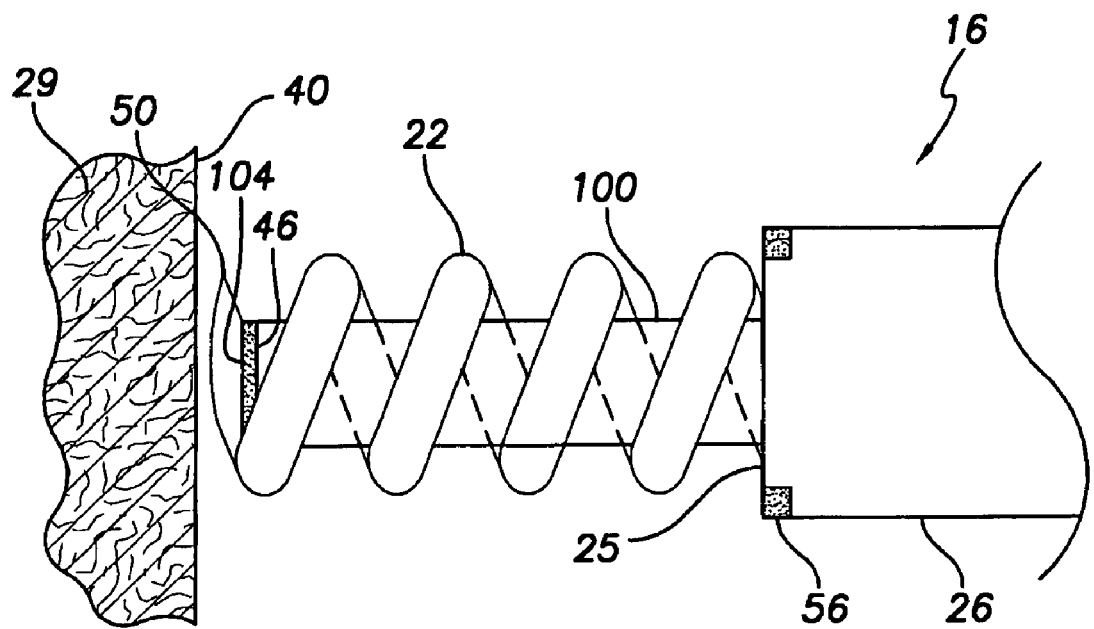
FIG. 11 is the same view as FIG. 7, except of another body embodiment.
Figure 12:
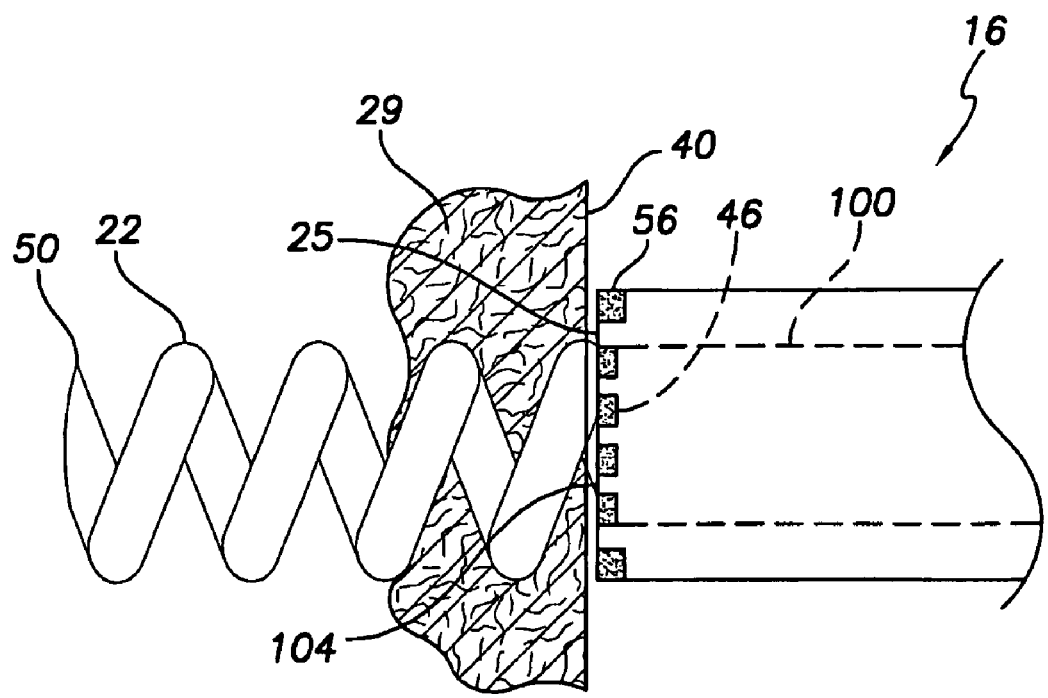
FIG. 12 is the same view as FIG. 8, except of another body embodiment.

The embodiments discussed with respect to FIGS. 7-10 concern bodies 100 that may have diameters sufficiently large to extend over the outer circumferences of the coils of the helical anchor 22. However, in other embodiments, the bodies 100 may be sufficiently small with respect to diameter that the bodies 100 may extend within the inner circumferences of the coils of the anchors. Such a configuration may be understood from FIGS. 11 and 12, which are the same respective views as FIGS. 9-10, except of another embodiment. As shown in FIG. 11, prior to being driven proximally by the cardiac tissue surface 40, the body 100 is in a distally extended state, the body 100 extending distally through the coils of the helical anchor 22. As indicated in FIG. 12, once the anchor 22 is fully embedded such that the cardiac tissue surface 40 has fully proximally driven the body distal end 104, the markers 46, 56 will be in close proximity (e.g., flush to each other), such close proximity being visible to the physician via fluoroscopy.

In some embodiments, the body 100 may not be biased, it instead being moved to the fully distal position of FIG. 11 by being in an interference relationship with the anchor 22 such that when the anchor 22 is distally displaced, the body 100 distally travels along with the anchor 22. The interference between the body 100 and anchor 22 is insufficient to prevent the body 100 from being proximally displaced relative to the anchor 22 when the body distal end 104 is acted upon by the cardiac tissue surface 40.

The body configurations discussed with respect to FIGS. 7-12 may be combined in a variety of ways. For example, anyone of configurations of the bodies 100 and biasing arrangements of FIGS. 7-12 may be configured such that the bodies 100 may be extendable within the inner circumferences of the anchor coils or extendable outside the outer circumferences of the anchor coils. Also, anyone of configurations of the bodies 100 and biasing arrangements of FIGS. 7-12 may be configured to be biased in manners similar to those discussed with respect to FIGS. 7-10 or non-biased similar to that discussed with respect to FIGS. 11-12.

As can be understood from the above discussion regarding FIGS. 2-12, the markers 44, 46 in the distal ends of the strips or body, as the case may be, appear via fluoroscopy to be near the tip of the helical anchor prior to the anchor tip beginning to embed in the cardiac tissue. As the helical anchor increasingly embeds in the cardiac tissue, the cardiac tissue surface abuts against and increasingly drives the distal end of the strips or body proximally. Once the helical anchor is fully embedded in the cardiac tissue, the distal end of the strips or body will be located near the distal end of the lead body housing, and the radiopaque markers in the end of the strips or body will appear via fluoroscopy to be near radiopaque markers in the distal end of the lead body housing, indicating to the physician that the helical anchor is fully embedded in the cardiac tissue.

As can be understood from FIGS. 2-12, a method for implanting an implantable active fixation medical lead may be as follows. First, the physician delivers the distal end 25 of a lead body 26 to the implantation site. The physician observes via fluoroscopy the presence of the radiopaque marker 44, 46 near a distal tip 50 of a helical anchor 22. The physician observes via fluoroscopy the proximal displacement of the radiopaque marker 44, 46 as the helical anchor 22 is screwed into cardiac tissue 29. The physician determines the helical anchor 22 is fully embedded in the cardiac tissue 29 when fluoroscopy reveals that the radiopaque marker 44, 46 has reached a location near the distal end 25 of the lead body 26. More specifically, in one embodiment, the physician determines the helical anchor 22 is fully embedded in the cardiac tissue 29 when fluoroscopy reveals that the radiopaque marker 44, 46 has reached a location near another radiopaque marker 56 in the distal end 25 of the lead body 26.

Although the present invention has been described with reference to preferred embodiments, persons skilled in the art will recognize that changes may be made in form and detail without departing from the spirit and scope of the invention.

What is claimed is:

1. An implantable medical lead for active fixation to cardiac tissue, the lead comprising:
   a lead body distal portion having a distal end;
   a tissue fixation helical anchor coupled to the lead body distal portion and including a distal tip; and
   a structure having a proximal end, a distal end and a body intermediate the proximal end and distal end, the structure extending distally from the lead body distal portion, the structure being moveable relative to the lead body distal portion, the proximal end of the structure extending outwardly from the lead body distal portion at a location proximal to the distal end of the lead body distal portion, the distal end of the structure having a first radiopaque marker, and the structure being biased to project the distal end of the structure near the distal tip;
   wherein, when the tissue fixation helical anchor is progressively embedded in the cardiac tissue, the cardiac tissue progressively displaces the distal end of the structure proximally.

2. The lead of claim 1, wherein, when the tissue fixation helical anchor is fully embedded in the cardiac tissue, the cardiac tissue has caused the distal end of the structure to be located near the distal end of the lead body distal portion.

3. The lead of claim 1, wherein the structure includes a protuberance.

4. The lead of claim 3, wherein the protuberance includes at least one of a strip, flap and arm.

5. The lead of claim 3, wherein the protuberance includes a stress concentration site that facilitates the protuberance deflecting in a desired direction.

6. The lead of claim 5, wherein the desired direction includes radially inward and proximally.

7. The lead of claim 5, wherein the desired direction includes radially outward and proximally.

8. The lead of claim 3, wherein the distal end of the structure is biased radially inward and distal.

9. The lead of claim 3, wherein the distal end of the structure is biased radially outward and distal.

10. The lead of claim 1, wherein the structure includes a pleated body.

11. The lead of claim 10, wherein the pleated body displaces at least one of over and within the tissue fixation helical anchor.

12. The lead of claim 1, wherein the structure includes a cylindrical body that generally displaces proximally as a whole when the distal end of the structure displaces proximally.

13. The lead of claim 12, wherein the cylindrical body displaces at least one of over and within the tissue fixation helical anchor.

14. The lead of claim 12, further comprising a biasing member that acts on the cylindrical body to bias the cylindrical body distally.

15. The lead of claim 1, further comprising a second radiopaque marker in the lead body distal portion.

16. The lead of claim 15, wherein the radiopaque marker includes at least one of platinum, tantalum, iridium, rhodium, tungsten and barium sulfate.

* * * * *